(12) United States Patent
Parietti et al.

(10) Patent No.: US 10,456,975 B2
(45) Date of Patent: Oct. 29, 2019

(54) MULTI-COMPARTMENT CAPSULE

(71) Applicant: Multiply Labs Inc., San Francisco, CA (US)

(72) Inventors: Federico Parietti, San Francisco, CA (US); Alice Melocchi, Dalmine (IT); Lucia Zema, Como (IT); Andrea Gazzaniga, Santa Giulietta (IT)

(73) Assignee: Multiply Labs Inc., San Francisco, CA (US)

( * ) Notice: Subject to any disclaimer, the term of this patent is extended or adjusted under 35 U.S.C. 154(b) by 0 days.

(21) Appl. No.: 15/625,833

(22) Filed: Jun. 16, 2017

(65) Prior Publication Data
US 2018/0015044 A1    Jan. 18, 2018

Related U.S. Application Data

(60) Provisional application No. 62/363,178, filed on Jul. 15, 2016.

(51) Int. Cl.
*B29C 64/118* (2017.01)
*B33Y 10/00* (2015.01)
(Continued)

(52) U.S. Cl.
CPC .......... *B29C 64/118* (2017.08); *A61K 9/4808* (2013.01); *A61K 9/4816* (2013.01); *B33Y 10/00* (2014.12); *B29L 2031/7174* (2013.01)

(58) Field of Classification Search
CPC .................................................. A61K 9/4808
See application file for complete search history.

(56) References Cited

U.S. PATENT DOCUMENTS

| 4,936,461 A | 6/1990 | Makiej et al. |
| 5,074,426 A | 12/1991 | Goodhart et al. |
| (Continued) | | |

FOREIGN PATENT DOCUMENTS

WO    WO 2004/010978 A1    2/2004

OTHER PUBLICATIONS

Pietrzak, Katarzyna, Abdullah Isreb, and Mohamed A. Alhnan. "A flexible-dose dispenser for immediate and extended release 3D printed tablets." European Journal of Pharmaceutics and Biopharmaceutics 96 (Aug. 12, 2015): 380-387. (Year: 2015).*

(Continued)

*Primary Examiner* — Benjamin A Schiffman
(74) *Attorney, Agent, or Firm* — Morgan, Lewis & Bockius LLP

(57) ABSTRACT

A method of making a capsule comprising a plurality of compartments, the method comprising: initiating extrusion of a filament solution through a filament extruder; laying the filament solution to form a base of the capsule; forming a first compartment in the plurality of compartments, wherein the forming creates a first barrier wall having a first predetermined release time; forming a second compartment in the plurality of compartments, wherein the forming creates a second barrier wall having a second predetermined release time; filling the first compartment with a first material; filling the second compartment with a second material; and sealing the plurality of compartments thereby forming the capsule with a first sealed compartment and a second sealed compartment.

29 Claims, 9 Drawing Sheets

(51) Int. Cl.
    *A61K 9/48*     (2006.01)
    *B29L 31/00*    (2006.01)

(56) References Cited

U.S. PATENT DOCUMENTS

| | | |
|---|---|---|
| 5,643,773 A | 7/1997 | Aebischer et al. |
| 7,163,693 B1 | 1/2007 | Clarke et al. |
| 7,670,612 B2 | 3/2010 | Miller |
| 8,361,497 B2 | 1/2013 | Miller |
| 2003/0049311 A1 | 3/2003 | McAllister et al. |
| 2006/0057201 A1 | 3/2006 | Bonney et al. |
| 2016/0120808 A1* | 5/2016 | Hoover .................. B33Y 10/00 427/2.14 |

OTHER PUBLICATIONS

International Search Report and Written Opinion for International Patent Application No. PCT/US2017/042430, dated Sep. 26, 2017, 10 pgs.

\* cited by examiner

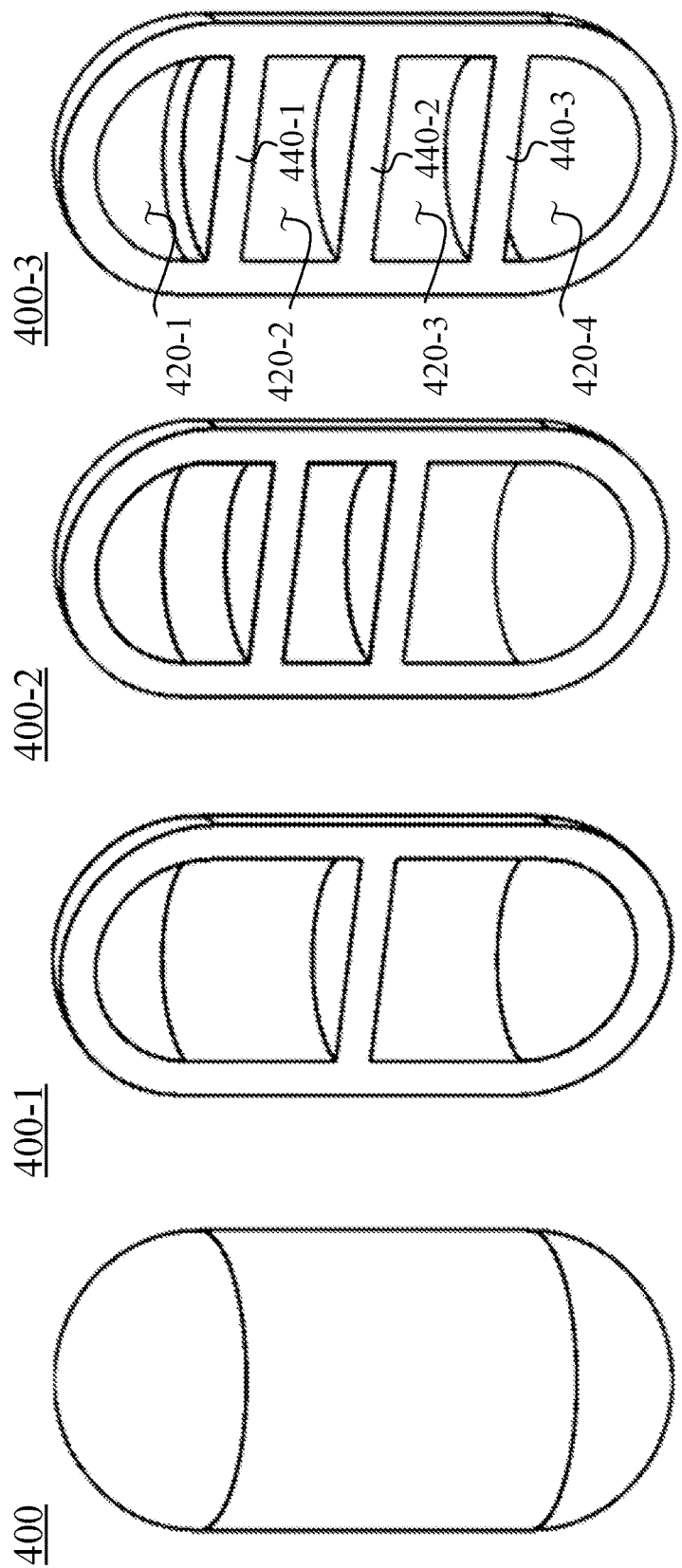

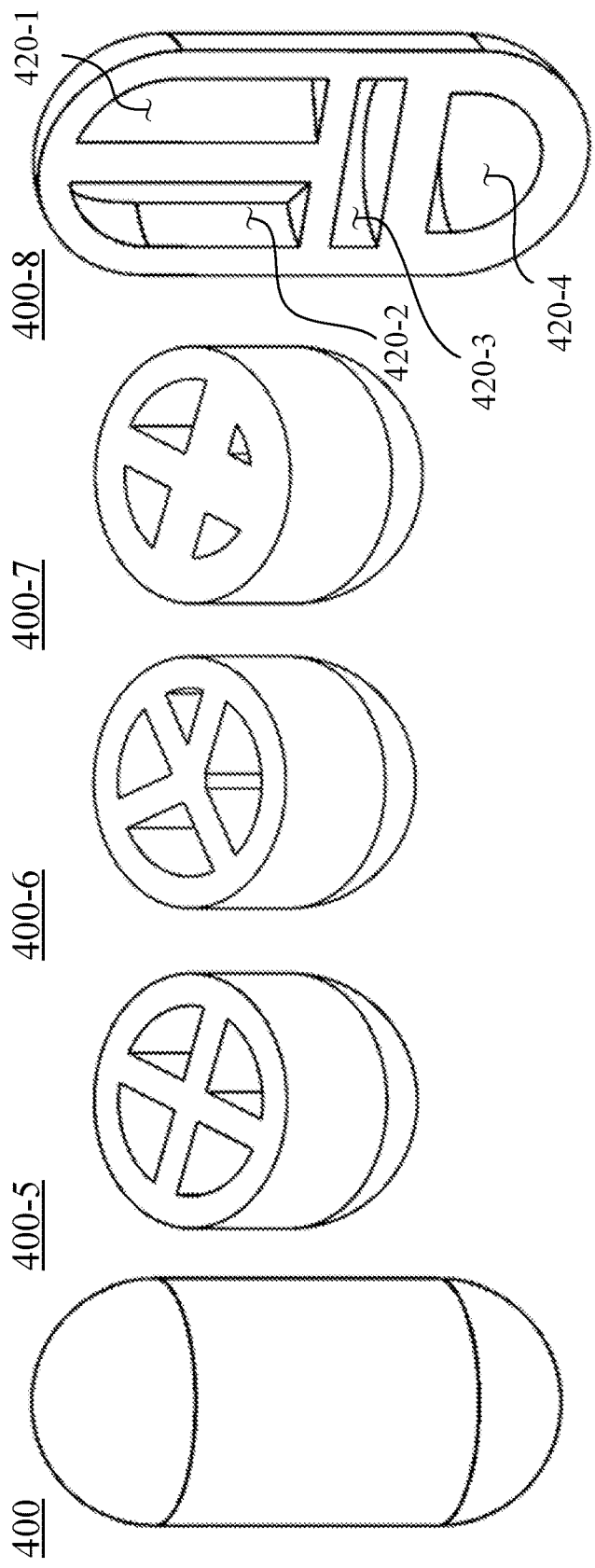

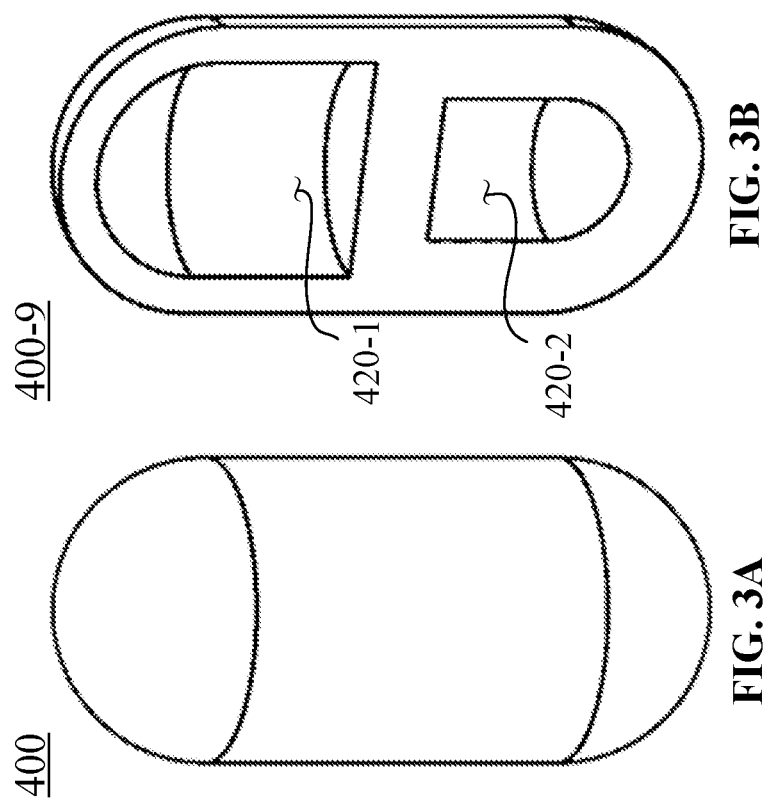

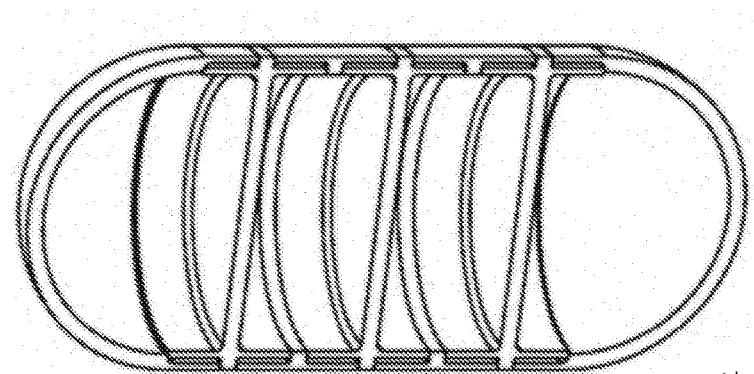
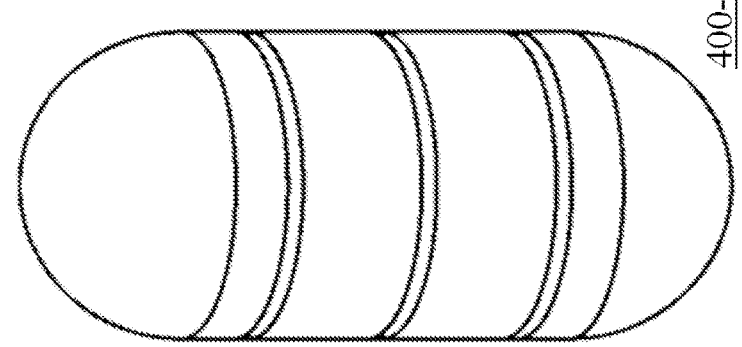
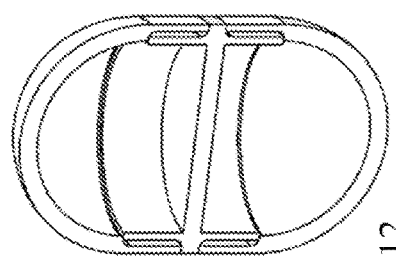
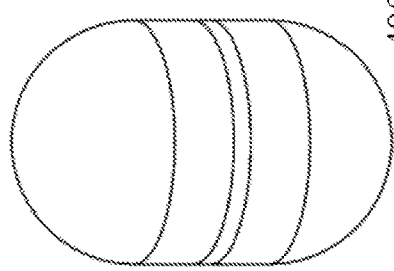
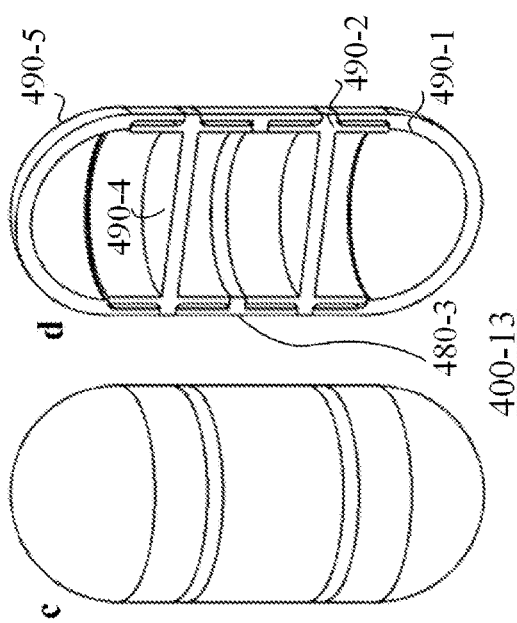
FIG. 5A  FIG. 5B  FIG. 5C  FIG. 5D  FIG. 5E  FIG. 5F

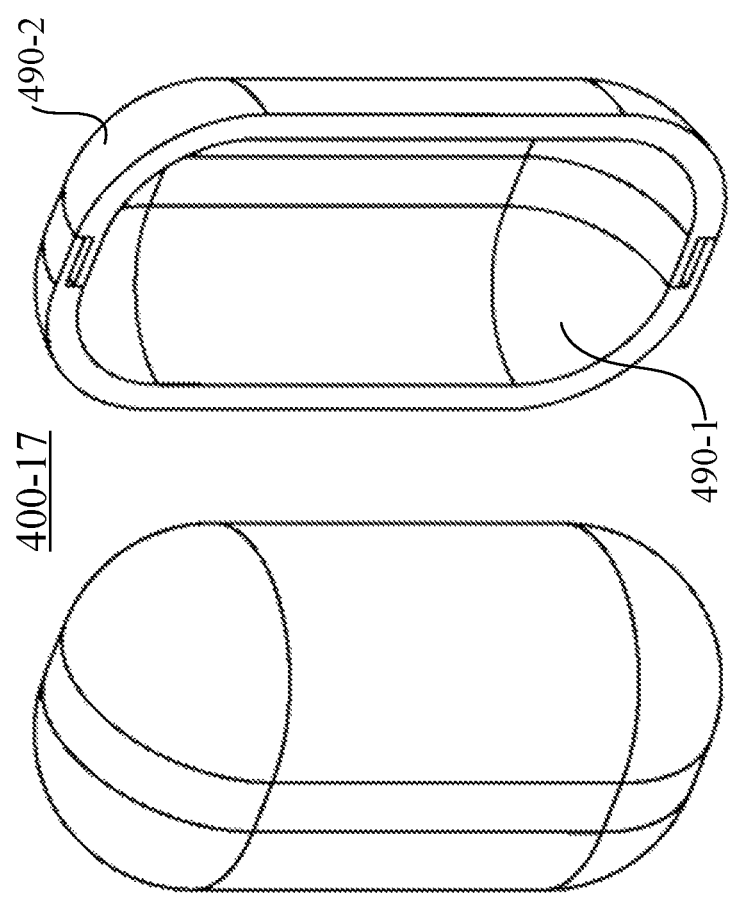

MULTI-COMPARTMENT CAPSULE

CROSS-REFERENCE(S) TO RELATED APPLICATION

This application claims priority to U.S. Provisional Patent Application No. 62/363,178 entitled "Multi-Compartment Functional Containers," filed on Jul. 15, 2016, to the entire contents of which is incorporated herein for all purposes by this reference.

TECHNICAL FIELD

The present disclosure generally relates to a multi-compartment capsule.

BACKGROUND

Oral administration is one of the most prevalent methods for delivering active ingredients or medicaments to the body. Active ingredients or medicaments may be orally administered in a variety of physical states such as solid, liquid, or powder. Capsules have become the preferred drug delivery systems (DDS) for administering oral dosages.

Conventional capsules include a first compartment section, known as a base, and a second compartment section referred to as a cap. The two compartments of the capsule are designed so that the material to be encapsulated is dispensed into the base, and the open end of the cap section is correspondingly disposed over the open end of the base. The walls of the cap and base are in physical contact with one another forming a single internal compartment. A means for structurally sealing the cap in relation to the base is also incorporated into the manufacturing of capsules, thereby preventing contamination of the capsule.

Advances in pharmacological therapy are achieved through the discovery of new molecules or the identification of more efficient methods of administration, e.g. the development of DDS. DDS exploits technological features, including design, composition, and manufacturing processes, to determine, modulate, and improve the drug availability at the site of action. In addition to the therapeutic advantages, DDS affords improvements in bioavailability, efficacy and compliance, as well as overall drug dose and side effect reduction. As such, the economic and health benefits related to the reduction and control of development costs and line extension through these improvements are important to the success of this technology.

A large number of encapsulates (carriers) used for DDSs are based on pharma-grade polymeric materials with a distinguishing behavior in the biological environment, including pH-dependent solubility, enzyme degradability, swelling (glassy to rubbery transition), and successive erosion and dissolution in aqueous fluids, bio-adhesion, and permeability. In some instances, the conventional DDS design strategy makes use of polymers inter-dispersed with the active ingredient in the form of a matrix system. In other instances, the conventional DDS design strategy applies the pharma-grade polymeric materials as a coating barrier onto active ingredient containing cores such as reservoir systems and osmotic pumps. In particular, for the coated systems, physical characteristics of the manufactured DDS pill, such as shape, dimension, and surface properties, as well as technological characteristics of thermal and mechanical resistance, friability, wettability, disintegration and dissolution tendency, and further stability characteristics of the inner core may impair or constrain the coating process and decrease on the system performance. Given the importance of DDS, new systems and methods for supporting DDS are needed in the art.

Given the above background, improvements regarding a dispensing system, a filament extruder, a capsule, and a user interface are needed in the art.

The information disclosed in this Background section is only for enhancement of understanding of the general background of the invention and should not be taken as an acknowledgement or any form of suggestion that this information forms the prior art already known to a person skilled in the art.

SUMMARY

The capsules detailed in the present disclosure address the shortcomings in the prior art detailed above.

Various aspects of the present disclosure are directed to providing a capsules which are configured to impart predetermined release (performance) metrics in accordance with engineered capsule compartment wall thickness, composition, and overall design of the capsule.

In accordance with an aspect of the present disclosure, the above and other objects can be accomplished by the provision of a method of making a capsule comprising a plurality of compartments.

In the method, the capsule is formed through the process of initializing extrusion of a filament solution through a filament extruder. The method further comprises laying the filament solution to form a base of the capsule and forming a first compartment in the plurality of compartments. The forming of the first compartment in the plurality of compartments creates a first barrier wall comprises a first predetermined release time. The method further comprises forming a second compartment in the plurality of compartments. The forming of the second compartment in the plurality of compartments creates a second barrier wall having a first predetermined release time. The method further comprises filling the first compartment with a first material and filling the second compartment with a second material. Moreover, the method further comprises sealing the plurality of compartments thereby forming the capsule with a first sealed compartment and a second sealed compartment.

The disclosed methods for making a capsule that has a plurality of compartments advantageously cures the disadvantages of the prior art while having the advantages of a plurality of compartments that are independently filled with one or more materials. The discloses capsules thereby impart predetermined release (performance) metrics in accordance with engineered capsule compartment wall thickness, composition, and overall design of the capsule.

The methods and apparatuses of the present disclosure have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 1A-FIG. 1D are views of the multi-compartment capsule according to an embodiment of the present disclosure;

FIG. 2A-FIG. 2E are views of the multi-compartment capsule according to another embodiment of the present disclosure;

FIG. 3A-FIG. 3B are views of the multi-compartment capsule according to another embodiment of the present disclosure;

FIG. 5A-FIG. 5F are views of the multi-compartment capsule according to another embodiment of the present disclosure;

FIG. 8A-FIG. 8B are views of the multi-compartment capsule according to another embodiment of the present disclosure.

Figures 4A, 4B, 4C:
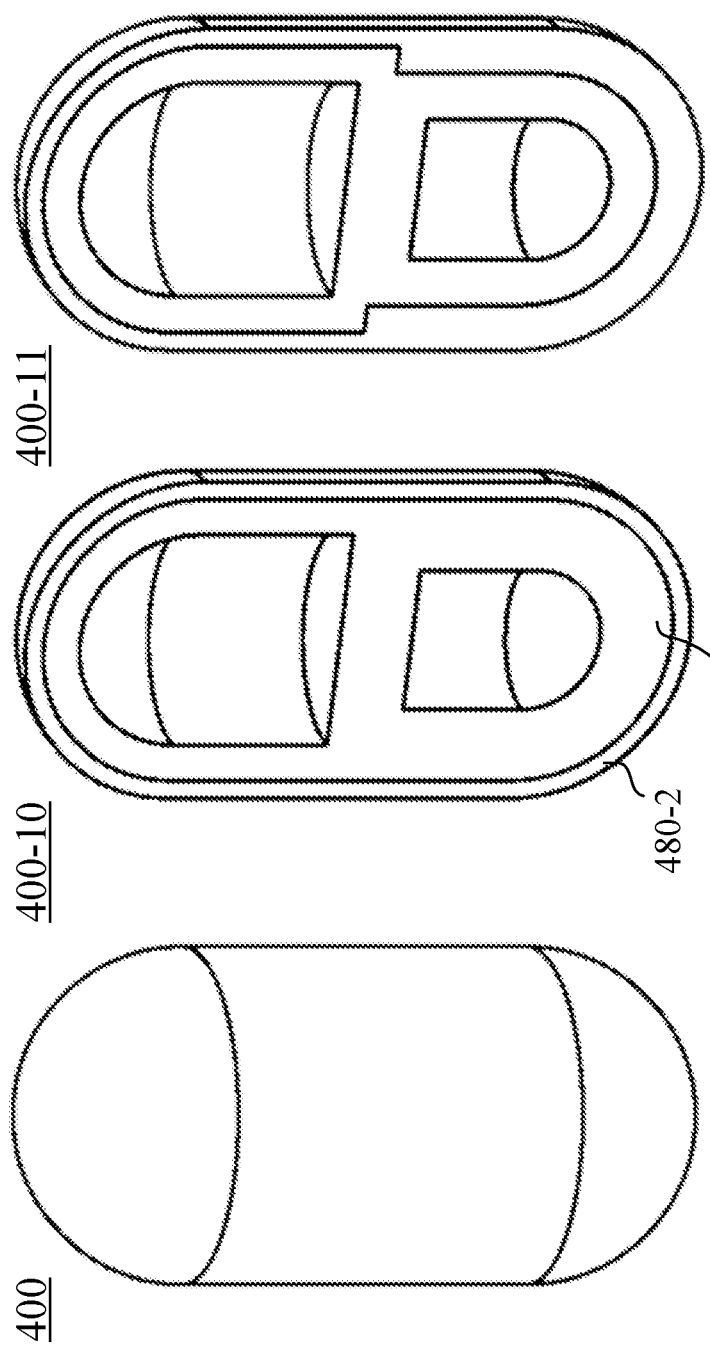
FIG. 4A-FIG. 4C are views of the multi-compartment capsule according to another embodiment of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawing and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the present invention as defined by the appended claims.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject" and "user" are used interchangeably herein.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and or "comprising," when used in this specification, specify the presence of stated features, integers, steps, operations, elements, and or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Various aspects of the present disclosure are directed to providing a method of making a capsule comprising a plurality of compartments. This capsule comprises a capsule 400 containing a plurality of compartments 420, in which encapsulating material 450 is enclosed. In one such embodiment in accordance with this aspect of the present disclosure, an extrusion of a filament solution is initiated. The filament solution is then laid down to form a base of the capsule 400. A first compartment 420-1 in the plurality of compartments 420 is formed. This forming creates a first barrier wall 440-1 having a first predetermined release time. A second compartment 420-2 in the plurality of compartments 420 is formed. This second forming creates a second barrier wall 440-2 having a second predetermined release time. The first compartment 420-1 is filled with a first material 460-1. The second compartment 420-2 is filed with a second material 460-2. The plurality of compartments 420 are then sealed thereby forming the capsule 400 with a first sealed compartment 420-1 and a second sealed compartment 420-2.

In some embodiments, the method of making a capsule 400 comprises forming the first and second compartments concurrently. In another embodiment, the first and second compartments are sequentially formed.

In further embodiments, the method of making a capsule 400 comprises performing the above steps without human intervention by an extrusion device (not shown) that is programmed with a first predetermined release time and the second predetermined release time.

In further embodiments, a first portion of the base is overlaid with a first interlocking surface 490-1, and the sealing forms a second interlocking surface 490-2 that joins the first interlocking surface 490-1. In other embodiments, a second portion of the base is overlaid with a third interlocking surface 490-3, and the sealing further forms a fourth interlocking surface 490-4 that joins the third interlocking surface 490-3. In still another embodiment, a third portion of the base is overload with a fifth interlocking surface 490-5, and the sealing forms a sixth interlocking surface 490-6 that joins the fifth interlocking surface 490-5. In still a further embodiment, the base comprises a first plurality of discrete interlocking surfaces 490-$n1$, and the sealing forms a second plurality of discrete interlocking surfaces 490-$n2$ and the sealing, for each respective discrete interlocking surface in the first plurality of discrete interlocking surfaces 490-$n1$, adjoins the respective discrete interlocking surface with a corresponding discrete interlocking surface in the second plurality of discrete interlocking surfaces 490-$n2$.

In the present disclosure, according to another aspect, the method of making the capsule 400 forms the capsule such that the base of the capsule comprises a first plurality of discrete interlocking surfaces 490. In such embodiments, the sealing forms a second plurality of interlocking surfaces 490 and, moreover, the sealing, for each respective discrete interlocking surface 490-1 in the first plurality of discrete interlocking surfaces 490, adjoins the respective discrete interlocking surface 490-1 with a corresponding discrete interlocking surface 490-2 in the second plurality of interlocking surfaces 490. The forming of the discrete interlocking surfaces 490 may comprise a separate injection molding process.

In some embodiments, the first predetermined release time is different than the second predetermined release time. For instance, in some embodiments, the first predetermined release time is less than five minutes and the second predetermined release time is greater than ten minutes. In another embodiment, the first predetermined release time is less than an hour and the second predetermined release time is greater than 2 hours. In yet another embodiment, the first release time is less than 30 minutes and the second release time is greater than an hour. In a further embodiment, the first predetermined release time ranges from 30 minutes to 4 hours and the second predetermined release time ranges from 6 hours to 18 hours. In some embodiments, the first predetermined release time is the same as the second predetermined release time.

In some embodiments, the first compartment 420-1 has a first barrier wall 440-1 formed of one or more vertical, horizontal, or radial walls; or the second compartment 420-2 has a second barrier wall 440-2 formed of one or more vertical, horizontal, or radial walls. According to the present disclosure, in another embodiment, the barrier walls 440 and the compartments 420 are formed in any number, size, and combination of vertical, horizontal, or radial walls.

Depending on the end design structure and goal, the plurality of barrier walls 440 are formed radially during a single extrusion process.

In some embodiments, the first material 480-1 is different than the second material 480-2. In another embodiment, the first material 480-1 is the same as the second material 480-2.

According to the present disclosure, the first predetermined release time is determined by a first characteristic of the first barrier wall 440-1. The first characteristic of the first barrier wall 440-1 comprises a thickness of the wall or porosity of the wall. Similarly, the second predetermined release time is determined by a first characteristic of the second barrier wall 440-2. The first characteristic of the second barrier wall 440-2 comprises a thickness of the wall or porosity of the wall. In some embodiments, the first barrier wall has a thickness less than 0.1 mm and the second barrier wall has a thickness greater than 0.2 mm. In another embodiment, the first barrier wall has a thickness less than 0.5 mm and the second barrier wall has a thickness greater than In yet another embodiment, the first barrier wall has a thickness that ranges from 0.01 mm to 0.5 mm and the second barrier wall has a thickness that ranges from 0.6 mm to 1 mm.

In some embodiments, the first characteristic of the first barrier wall 440-1 comprises a pH sensitive material. Similarly, the second predetermined release time is determined by a first characteristic of the second barrier wall 440-2. The first characteristic of the second barrier wall 440-2 comprises a different pH sensitive material, so that the second barrier wall 440-2 decomposes at a pH different than the first barrier wall 440-1.

In some embodiments, the first sealed compartment 420-1 has a volume that is different than the second sealed compartment 420-2. In another embodiment, the first sealed compartment 420-1 has a volume that is the same as the second sealed compartment 420-2. In another embodiment, the first sealed compartment has a volume less than 0.5 mL and the second sealed compartment has a volume greater than 0.6 mL. In yet another embodiment, the first sealed compartment has a volume less than 0.05 mL and the second sealed compartment has a volume greater than 1 mL. In a further embodiment, the first sealed compartment has a volume that ranges from 0.01 mL to 0.2 mL and the second sealed compartment has a volume that ranges from 0.2 mL to 0.5 mL.

Other embodiments of the present disclosure comprise the method of making a capsule 400, wherein the plurality of compartments 420 comprises three or more compartments 420-3 to 420-n.

The shape of the capsule 400 is defined by the shape and number of compartments 420; however, the capsule 400 may comprise a predetermined shape that is stored in a controller or a software (not shown). The present predetermined shape comprises an hourglass, an ellipsoid, or a cylinder with hemispheres. However, the present disclosure is not limited thereto. For instance, the predetermined shape may be a non-uniform shape. In a further embodiment, the predetermined shape is asymmetric about one or more axes enabling the user to determine the orientation of the capsule 400 by touch. Also, according to the present disclosure, in another embodiment the capsule's 400 comprise a shape or a volume controlled by a predetermined algorithm or a software.

In some embodiments, the thickness of the walls ranges from 0.1 mm to 2 mm. In other embodiments, the volume of the compartments 420 ranges from 0.1 mL to 2 mL.

In another embodiment of the present disclosure, the external walls of the capsule 400 are formed with a textured surface. The textured surface comprises a dimple configured to enable a user differentiate the orientation of the capsule 400 of individual capsules from a plurality of capsules. In an even further embodiment, the textured surface is configured to allow the capsule 400 to bind to a food product.

Additionally, in further embodiments of the present disclosure, the capsule 400 comprises the first material 480-1 is any one from the group comprising: ethyl cellulose, hydroxypropyl cellulose, hydroxypropyl methyl cellulose, hydroxypropyl methyl cellulose acetate succinate, various types of methacrylic acid copolymers, polyethylene oxide, polyvinyl alcohol, polyvinyl alcohol-polyethylene glycol graft copolymer, and polyvinyl caprolactam-polyvinyl acetate-polyethylene glycol graft co-polymer; or the capsule 400 comprises the second material 480-2 is any one from the group comprising: ethyl cellulose, hydroxypropyl cellulose, hydroxypropyl methyl cellulose, hydroxypropyl methyl cellulose acetate succinate, various types of methacrylic acid copolymers, polyethylene oxide, polyvinyl alcohol, polyvinyl alcohol-polyethylene glycol graft copolymer, and polyvinyl caprolactam-polyvinyl acetate-polyethylene glycol graft co-polymer.

Figure 6A:
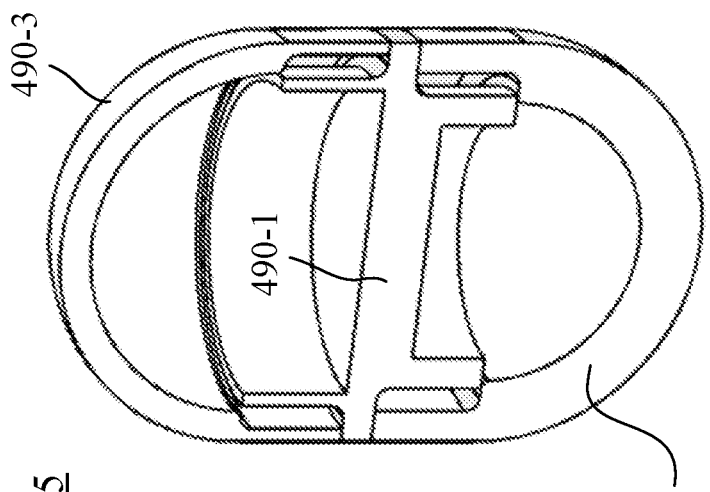
FIG. 6A-FIG. 6B are views of the multi-compartment capsule according to another embodiment of the present disclosure.
Figure 6B:
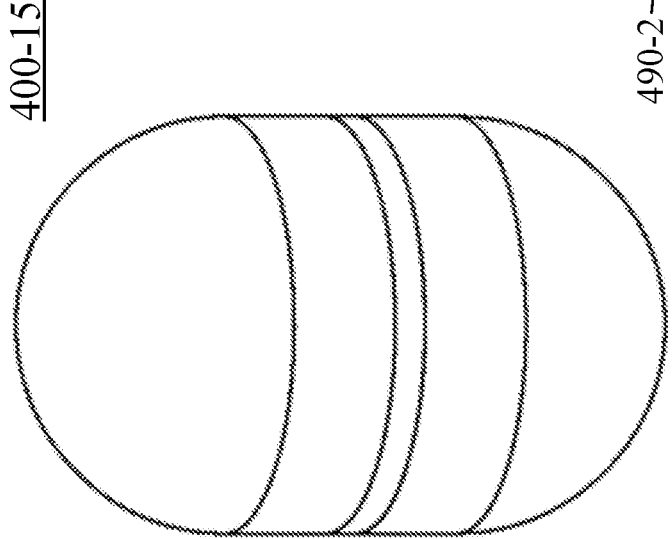
Figures 7A, 7B:
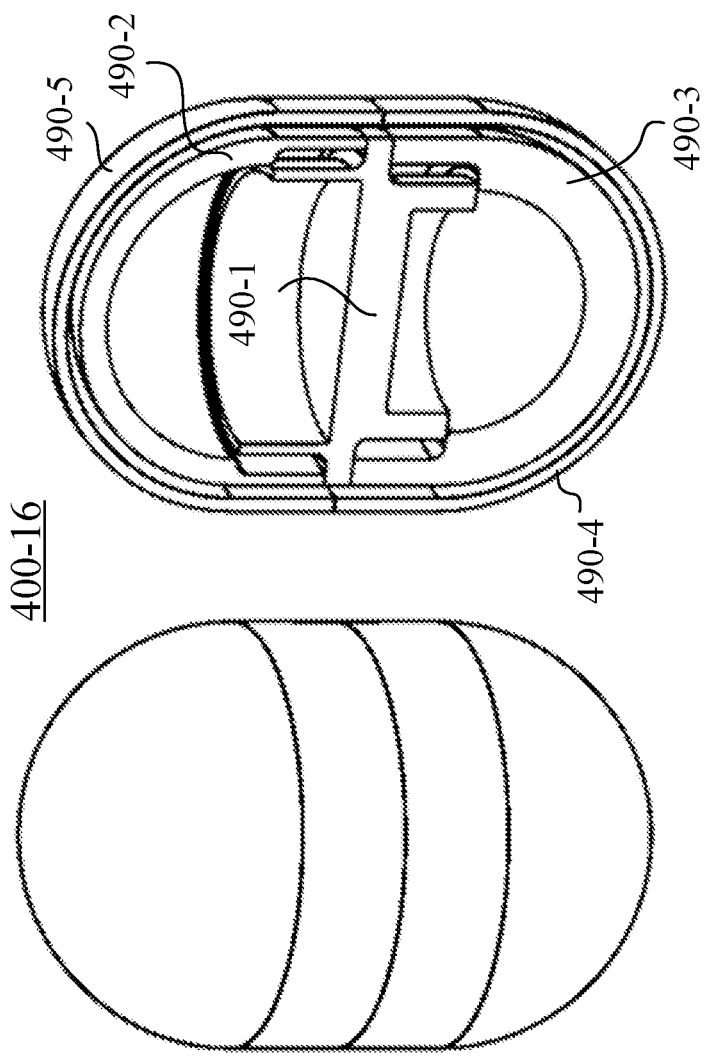
FIG. 7A-FIG. 7B are views of the multi-compartment capsule according to another embodiment of the present disclosure.
Figure 9D:
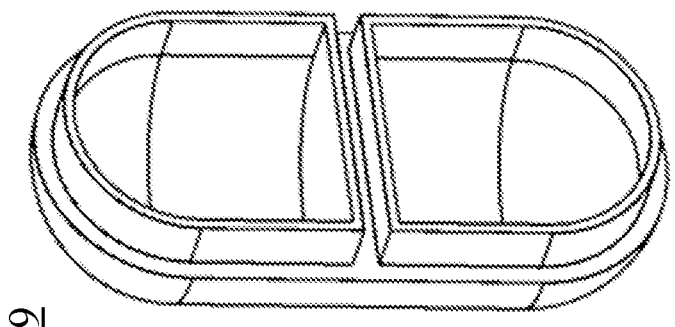
FIG. 9A-FIG. 9D are views of the multi-compartment capsule according to another embodiment of the present disclosure.
Figure 9C:
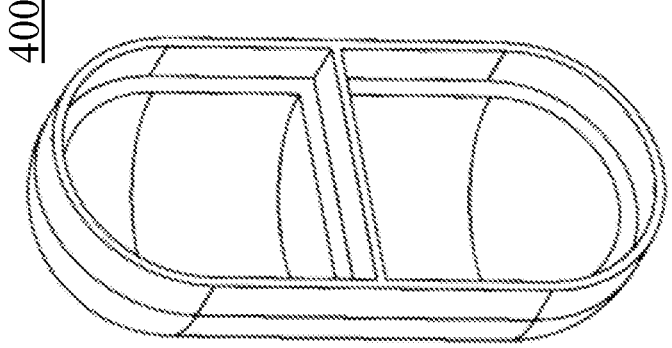
Figure 9B:
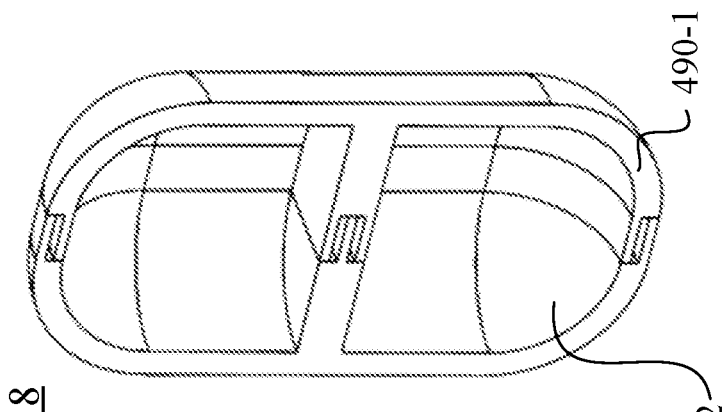
Figure 9A:
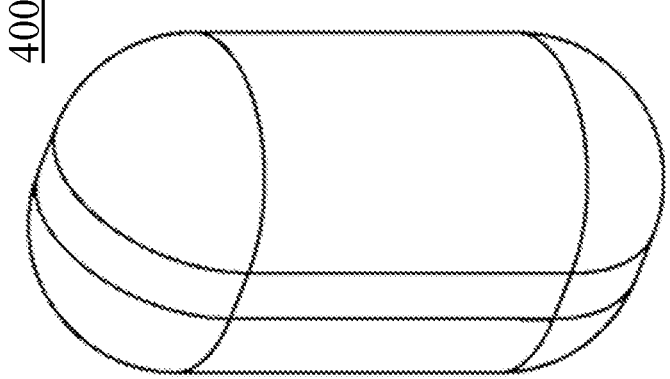

Referring to FIG. 1A through FIG. 9D, exemplary embodiments of the present disclosure are provided. As shown in FIG. 1A through FIG. 4C, an exemplary embodiment of the present disclosure comprises a plurality of compartments 420, a plurality of barrier walls 440, a plurality of filling material 460, or a plurality of capsule material 480. FIG. 5A through FIG. 9D depict other embodiments of the present disclosure wherein a plurality of interlocking surfaces 490 are formed.

Accordingly, a method of making a capsule comprising a plurality of compartments, according to an exemplary embodiment of the present disclosure, addresses the deficiencies of the prior art while having the advantages of comprising a plurality of materials capable of imparting a release performance according to the thickness, composition, and design of the capsule.

For convenience in explanation and accurate definition in the appended claims, the terms "upper", "lower", "up", "down", "upwards", "downwards", "inner", "outer", "inside", "outside", "inwardly", "outwardly", "interior", "exterior", "front", "rear", "back", "forwards", and "backwards" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various alternatives and modifications thereof. It is intended that the scope of the invention be defined by the Claims appended hereto and their equivalents.

What is claimed is:

1. A method of making a capsule for encapsulating one or more materials, comprising a plurality of compartments, the method comprising:
   A) initiating extrusion of a filament melt through a filament extruder, wherein the filament is free of the one or more materials;
   B) laying the filament melt with the filament extruder to form a base of the capsule;
   C) forming a first compartment in the plurality of compartments by laying of the filament melt with the filament extruder, wherein the forming C) creates a first barrier wall, wherein the first barrier wall:
      i) has a first predetermined release time, and
      ii) separates the first compartment in the plurality of compartments from one or more different compartments in the plurality of compartments;
   D) filling the first compartment with a first material of the one or more materials;
   E) sealing the first compartment by laying of the filament melt with the filament extruder;
   F) forming a second compartment in the plurality of compartments by laying of the filament melt with the filament extruder on a portion of the first barrier wall, wherein the forming F) creates a second barrier wall, wherein the second barrier wall:
      i) has a second predetermined release time, and
      ii) separates the second compartment in the plurality of compartments from one or more different compartments in the plurality of compartments;
   G) filling the second compartment with a second material of the one or more materials; and
   H) sealing the second compartment thereby forming the capsule with a first sealed compartment and a second sealed compartment, wherein:
      the initiating A), laying B), forming C), sealing E), forming F), and sealing H) are performed without human intervention by an extrusion device that is programmed with the first predetermined release time and the second predetermined release time.

2. The method of claim 1, wherein the forming C) and forming F) and performed concurrently.

3. The method of claim 1, wherein the forming C) and forming are performed sequentially.

4. The method of claim 1, wherein the first predetermined release time is different than the second predetermined release time.

5. The method of claim 1, wherein the first predetermined release time is the same as the second predetermined release time.

6. The method of claim 1, wherein the first material is different than the second material.

7. The method of claim 1, wherein the first material is the same as the second material.

8. The method of claim 1, wherein the first predetermined release time is determined by a first characteristic of the first barrier wall.

9. The method of claim 8, wherein the first characteristic is a thickness of the first barrier wall or a porosity of the first barrier wall.

10. The method of claim 1, wherein the second predetermined release time is determined by a first characteristic of the second barrier wall.

11. The method of claim 10, wherein the first characteristic is a thickness of the second barrier wall or a porosity of the second barrier wall.

12. The method of claim 1, wherein the plurality of compartments comprises three or more compartments.

13. The method of claim 1, wherein the first sealed compartment has a volume that is different than the second sealed compartment.

14. The method of claim 1, wherein the first sealed compartment has a volume that is the same as second sealed compartment.

15. The method of claim 1, wherein the capsule has a shape and volume that is controlled by a predetermined algorithm or software.

16. The method of claim 15, wherein the predetermined shape is asymmetric about one or more axes or non-uniform, enabling the user to determine the orientation of the capsule by touch.

17. The method of claim 1, wherein a first portion of the base is overlaid with a first interlocking surface, and wherein the sealing E) or sealing H) forms a second interlocking surface that joins the first interlocking surface.

18. The method of claim 17, wherein a second portion of the base is overlaid with a third interlocking surface, and wherein the sealing E) or sealing H) further forms a fourth interlocking surface that joins the third interlocking surface.

19. The method of claim 18, wherein a third portion of the base is overlaid with a fifth interlocking surface, and wherein the sealing E) or sealing H) further forms a sixth interlocking surface that joins the fifth interlocking surface.

20. The method of claim 1, wherein
   the base comprises a first plurality of discrete interlocking surfaces,
   the sealing E) or sealing H) forms a second plurality of discrete interlocking surfaces, and
   the sealing E) or sealing H), for each respective discrete interlocking surface in the first plurality of discrete interlocking surfaces, adjoins the respective discrete interlocking surface with a corresponding discrete interlocking surface in the second plurality of discrete interlocking surfaces.

21. The method of claim 20, the method further comprising making each discrete interlocking surface in the first plurality of discrete interlocking surfaces or second plurality of discrete interlocking surfaces is formed during a separate injection molding process.

22. The method of claim 1, wherein the first compartment has a first internal wall formed of one or more vertical, horizontal, or radial walls.

23. The method of claim 1, wherein
the capsule is characterized by a first central plane,
each compartment in the plurality of compartments is defined by a different set of internal walls in a plurality of sets of internal walls, and
each internal wall in each respective set of internal walls in the plurality of internal walls is disposed vertically, horizontally, or a radially with respect to the first central plane.

24. The method of claim 1, wherein the capsule comprises a plurality of barrier walls, wherein the plurality of barrier walls includes the first barrier wall and the second barrier wall, and the plurality of barrier walls is formed radially during a single extrusion process.

25. The method of claim 1, wherein the capsule is formed (i) from a single part without joints, (ii) using one or more locking components, or (iii) from a plurality of separate components.

26. The method of claim 1, wherein the capsule is characterized by one or more external surfaces, and the method further comprises imparting a textured surface on the one or more external surfaces of the capsule.

27. The method of claim 1, wherein a thickness of the first barrier wall or the second barrier wall is between 0.1 mm and 5 mm.

28. The method of claim 1, wherein a volume of the first compartment or the second compartment is between 1 mm$^3$ and 3000 mm$^3$.

29. The method of claim 1, wherein the first material or the second material are selected from the group consisting of: ethyl cellulose, hydroxypropyl cellulose, hydroxypropyl methyl cellulose, hydroxypropyl methyl cellulose acetate succinate, various types of methacrylic acid copolymers, polyethylene oxide, polyvinyl alcohol, polyvinyl alcohol-polyethylene glycol graft copolymer, and polyvinyl caprolactam-polyvinyl acetate-polyethylene glycol graft co-polymer.

* * * * *